US006468217B1

(12) United States Patent
Fazioli

(10) Patent No.: US 6,468,217 B1
(45) Date of Patent: Oct. 22, 2002

(54) METHOD AND APPARATUS FOR PERFORMING REAL-TIME STORAGE OF ULTRASOUND VIDEO IMAGE INFORMATION

(75) Inventor: Theodore P Fazioli, Salem, NH (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 09/902,341

(22) Filed: Jul. 10, 2001

(51) Int. Cl.[7] .................................................. A61B 8/00
(52) U.S. Cl. ........................................................ 600/443
(58) Field of Search ................................. 600/437, 443, 600/447

(56) References Cited

U.S. PATENT DOCUMENTS

| 5,322,066 | A | * | 6/1994 | Miyataka et al. | 600/437 |
| 5,740,801 | A | * | 4/1998 | Branson | 128/920 |
| 5,795,297 | A | * | 8/1998 | Daigle | 600/447 |
| 5,949,491 | A | * | 9/1999 | Callahan et al. | 600/437 |
| 6,210,327 | B1 | * | 4/2001 | Brackett et al. | 600/437 |
| 6,213,944 | B1 | * | 4/2001 | Miller et al. | 600/437 |
| 6,231,508 | B1 | * | 5/2001 | Miller et al. | 600/437 |
| 6,231,510 | B1 | * | 5/2001 | Negrin et al. | 600/443 |
| 6,262,749 | B1 | * | 7/2001 | Finger et al. | 128/916 |
| 6,263,094 | B1 | * | 7/2001 | Rosich et al. | 382/128 |

* cited by examiner

Primary Examiner—Francis J. Jaworski
(74) Attorney, Agent, or Firm—John Vodopia

(57) ABSTRACT

A method and apparatus are provided for storing digitized video ultrasound images in a digital memory device to enable high quality ultrasound video images to be stored in real-time. The ultrasound image acquisition and video storage system of the present invention comprises an ultrasound image acquisition component and a digital video storage component. The ultrasound image acquisition component logic acquires ultrasound images over a period of time and converts them into digital video images in real-time as the images are acquired. The digital video storage logic obtains the digital video images from the ultrasound image acquisition component and stores the digital video images in a digital storage device in real-time.

22 Claims, 4 Drawing Sheets

METHOD AND APPARATUS FOR PERFORMING REAL-TIME STORAGE OF ULTRASOUND VIDEO IMAGE INFORMATION

TECHNICAL FIELD OF THE INVENTION

The present invention relates to ultrasound imaging and, more particularly, to a method and apparatus for performing real-time storage of video ultrasound images as the images are being acquired.

BACKGROUND OF THE INVENTION

Existing ultrasound systems use videocassette recorders (VCRs) to record and playback lengthy live ultrasound imaging sessions. One problem associated with using VCRs for this purpose is that VCR images are generally of poor image quality. VCR recordings have relatively small dynamic color ranges and low resolution. Moreover, the magnetic VCR tapes degrade over time and are bulky, which are issues that present difficulties when considering how to archive the ultrasound images and how to manage the archived ultrasound images. Another problem associated with videocassette recordings is that the stored images are difficult to convert into other image storage formats and to transfer to other types of storage media. For example, it would be difficult, in terms of the additional hardware and software, to convert VCR ultrasound images into digitally formatted images that could be transferred over a network, such as the Internet, for storage in an on-line database.

In some ultrasound systems, video images are acquired digitally and stored to a storage medium, such as a magnetic disk. However, such systems are used in situations where the image acquisition time is relatively small, i.e., they are not used for lengthy ultrasound imaging sessions. Also, in these systems, the amount of time required to store the digital ultrasound image information is greater than the amount of time required to acquire the ultrasound image information. Thus, storage of the digital ultrasound image information does not occur in real-time. Consequently, this type of configuration is not suitable for storing lengthy ultrasound imaging sessions in real-time.

It would be advantageous to provide the ability to store high-quality digital ultrasound images as they are acquired in real-time and in such a way that the images can be easily and efficiently archived and managed. Convenient and efficient archiving of digital ultrasound images would, in turn, allow high quality digital ultrasound images that have been acquired and stored in real-time to be later accessed in their time-registered digital format. Accordingly, a need exists for a method and apparatus for performing real-time storage of video ultrasound images as the images are being acquired.

SUMMARY OF THE INVENTION

The present invention provides a method and apparatus for storing digitized video ultrasound images in a digital memory device to enable high quality ultrasound video images to be stored in real-time. The apparatus of the present invention is an ultrasound image acquisition and video storage system that comprises an ultrasound image acquisition component and a digital video storage component. The ultrasound image acquisition component logic acquires ultrasound images over a period of time and converts them into digital video images in real-time as the images are acquired. The digital video storage logic obtains the digital video images from the ultrasound image acquisition component and stores the digital video images in a digital storage device in real-time.

The method of the present invention for storing digital video ultrasound images comprises the steps of acquiring ultrasound images over a period of time, converting the acquired ultrasound images into digital video images in real-time as the images are acquired, and storing the digital video images in a digital storage device in real-time.

These and other features and advantages of the present invention will become apparent from the following description, drawings and claims.

DETAILED DESCRIPTION OF THE INVENTION

Digital recording systems are becoming available that include disk drives that have the capacity for storing digitized video data. High-speed data acquisition systems are also becoming available that allow real-time, or "live", storage of digitized video data to a disk. The combination of these technological advancements now makes it possible to store long imaging sessions in digital form in real-time. In accordance with the present invention, it has been determined that it is possible to combine these technological advancements with ultrasound imaging technology to enable high quality ultrasound images to be easily and conveniently digitally archived and managed.

Figure 1:
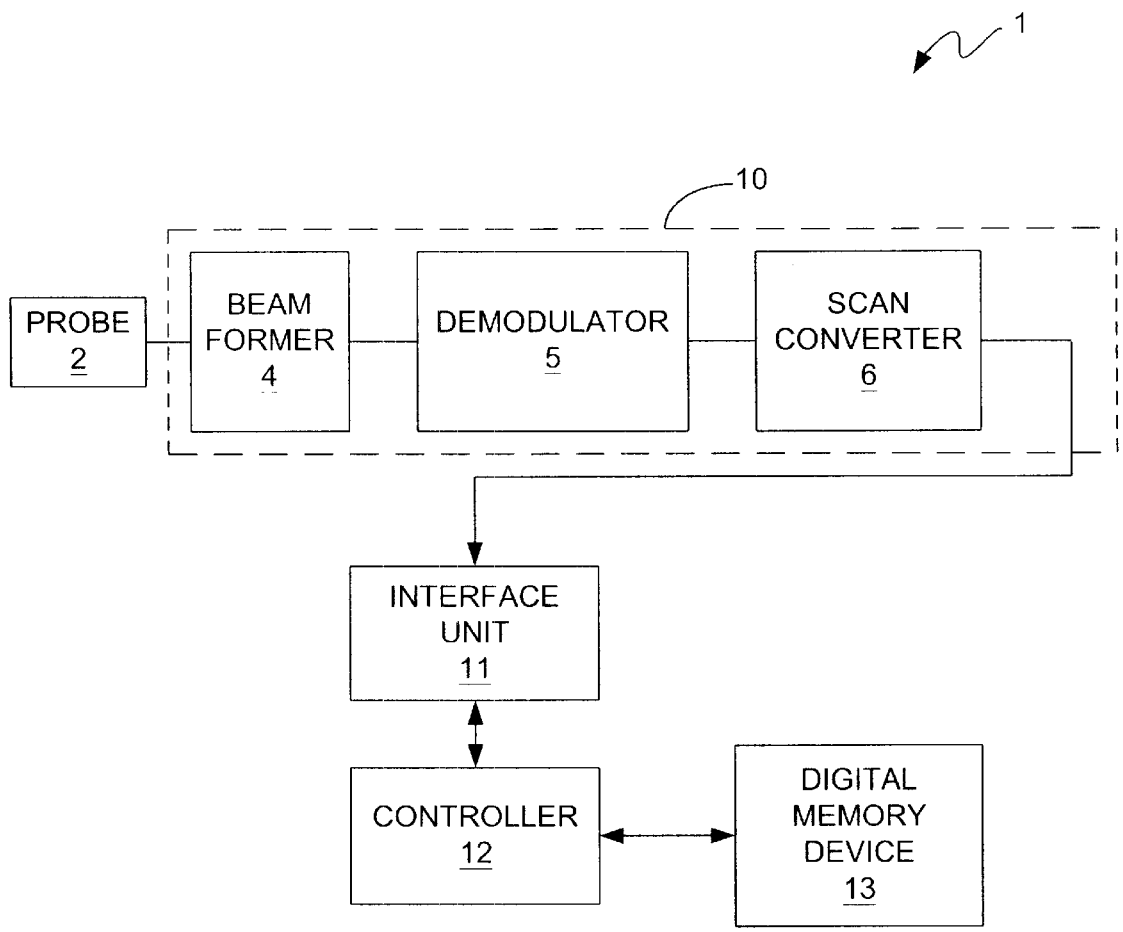
FIG. 1 is a block diagram of the ultrasound image acquisition and video storage (UIAVS) system of the present invention in accordance with one an example embodiment.

FIG. 1 is a block diagram of the ultrasound image acquisition and video storage (UIAVS) system 1 of the present invention in accordance with an example embodiment. In accordance with this embodiment, a high-speed data acquisition component is employed in an ultrasound device and is utilized in conjunction with a digital memory device having a relatively large storage capacity to enable real-time storage of digitized video data to the digital memory device. The (UIAVS) system 1 comprises ultrasound image acquisition circuitry 10 that acquires real-time acoustic ultrasound image data from a patient (not shown) via an ultrasound probe 2 and converts the ultrasound image information into real-time digital video ultrasound information. The real-time digital video ultrasound information is received by an interface unit 11 that temporarily stores the real-time digital video ultrasound information and synchronizes the information to the timing of a controller 12, which may be a processor, such as a microprocessor, for example. As the video information is received and synchronized by the interface unit 11, the controller 12 obtains the video information and stores it in a digital memory device 13.

The digital memory device 13 is a memory device that is capable of being written to at high speed so that the real-time nature of the acquired video information is preserved and can be played back on a display device (not shown) at a later time as a real-time video recording. The digital memory device 13 may be, for example, a hard drive memory device of the type used with many computer systems, since hard drive memory devices are typically capable of storing large amounts of digital video data at high speeds. The memory device 13 may also simply be one of a bank of such storage devices used for storing and archiving digital information. By storing the ultrasound video information in this manner, high quality videos of ultrasound imaging sessions, which may be of long or short time duration, can be archived for viewing at a later time. Furthermore, the possibility that the image quality of the archived videos might degrade is minimized or eliminated by using a digital storage medium.

Before further describing the manner in which the present invention enables high quality digital video images to be archived for later viewing, the manner in which the ultrasound image acquisition circuitry 10 operates will be described. The ultrasound image acquisition circuitry 10 is electrically coupled to the probe, or transducer, 2. The ultrasound image acquisition circuitry 10 comprises a beam former component 4 that generates electrical signals that cause the probe 2 to form a shaped acoustic beam. The probe 2 projects the acoustic beam into the patient. Reshaped acoustic waves that are back scattered (i.e., echoes) by discontinuities in the patient's body are returned to the probe 2, which reconverts them into electrical signals.

These signals are beam formed by the beam former component 4 and demodulated by a demodulator component 5. The ultrasound waves that are generated by the probe 2 normally are high frequency waxes. Therefore, the acoustic waves back scattered by discontinuities in the patient's body are also high frequency waves. However, the information that is of interest in the back scattered acoustic waves corresponds to relatively low frequency variations in the amplitude of the back scattered acoustic waves over time. The demodulator component 5 separates these amplitude variations from the high frequency ultrasound signal and generates an envelope signal, which corresponds to these amplitude variations over time. The scan converter component 6 receives the envelope signal from the demodulator component 5 and allocates digital pixel intensity values for pixels of an image frame, which is stored in an image memory comprised by the scan converter component 6.

As the acoustic beam is steered in different directions by the beam former component 4, i.e., as the angle of projection of the beam is incrementally shifted, different pixels in the frames of the scan converter image memory are filled in with image data. If it was deemed desirable to view these video images, video output circuitry (not shown) could be used at this point in the process to read the image frames out of the scan converter image memory and cause them to be displayed on a display monitor (not shown). Each line would be comprised of a series of pixels and each point along a line corresponds to a particular depth into the patient as measured from the center of the probe surface. However, since the present invention is directed to storing and archiving these video images, the video output circuitry and display monitor are not shown in FIG. 1.

Each page of the scan converter image memory contains the data for one image frame. The image memory component of the scan converter 6 typically contains many image frames of the object within the patient being imaged. These image frames are output to the interface unit 11 and are stored in the digital memory device 13. The interface unit 11 may be, for example, a Peripheral Component Interconnect (PCI) device comprising a Direct Memory Access (DMA) component that enables the interface unit 11 to directly write and read the digital video image data to and from the digital memory device 13 without the need for involving the controller 12 in this process. On the other hand, if image processing, such as digital video compression/decompression is to be performed, the controller 12 would be needed to perform these processes. In this latter case, the interface unit 11 could simply be a PCI device that interfaces the controller 12 to the ultrasound image acquisition circuitry 10 and synchronizes the data output from the scan converter component 6 with the timing of the controller 12. The controller 12 would then control the reading and writing of the video image information to the digital memory device 13.

Figure 2:
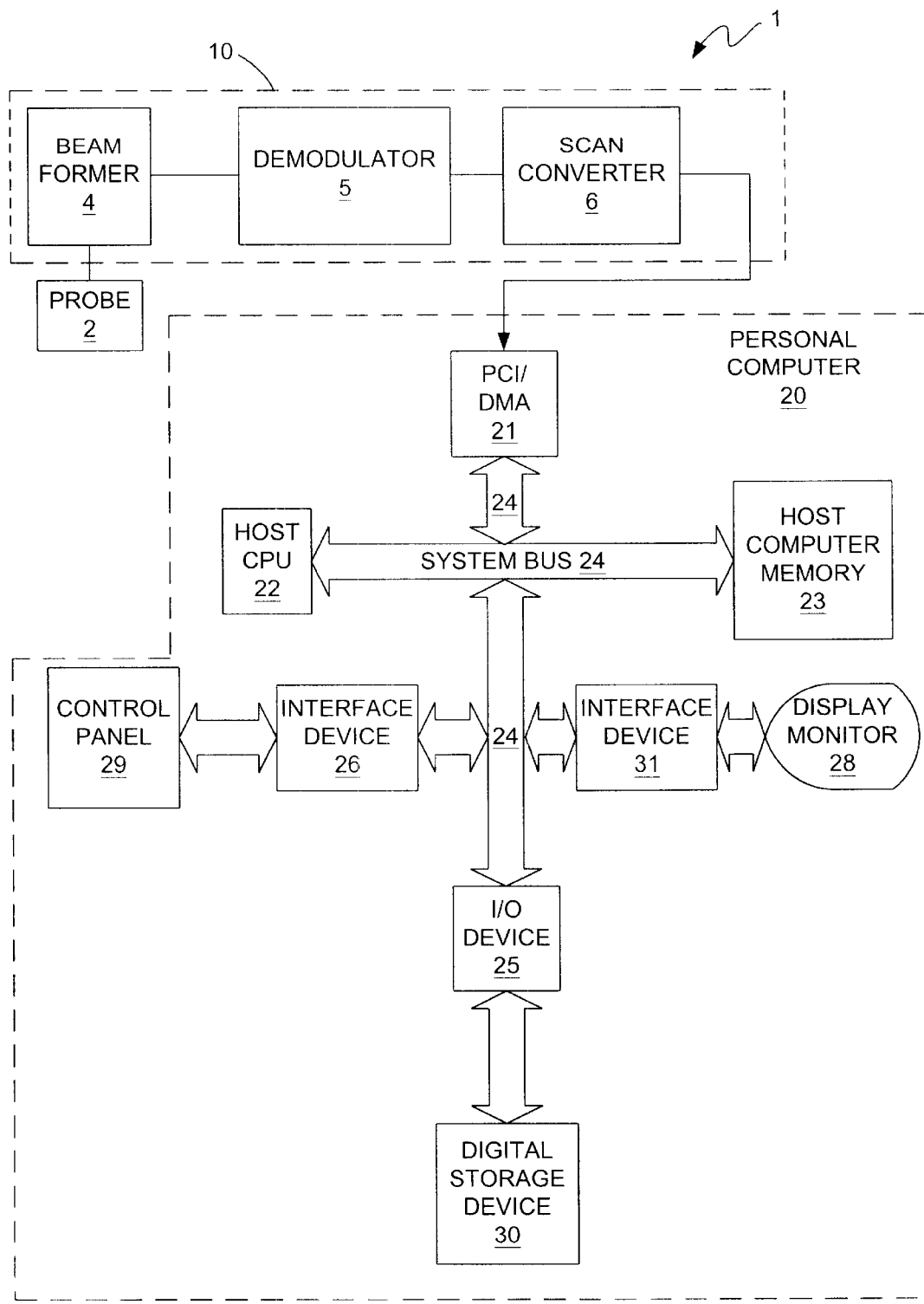
FIG. 2 is a block diagram of the ultrasound image acquisition and video storage (UIAVS) system of the present invention in accordance with one another example embodiment.

FIG. 2 illustrates another example embodiment of the present invention in which the ultrasound image acquisition circuitry 10 is in communication with a personal computer 20. Therefore, in this case, the UIAVS system 1 of the present invention comprises the ultrasound image acquisition circuitry 10 and the personal computer 20. The hard drive of the PC is used to store the digitized video images. The operations of the ultrasound image acquisition circuitry 10 and the probe 2 may be identical to the operations of those components described with reference to FIG. 1. Therefore, the operations of those components will not be further described. The interface unit 11 shown in FIG. 1 is comprised as a PCI/DMA device 21. The PCI/DMA device 21 receives the digital video image frames from the scan converter component 6 and temporarily stores it in the host computer memory 23, which may be a Random Access Memory (RAM) device, for example. By using the PCI/DMA device 21, the host central processing unit (CPU) 22 of the personal computer 22 is free of having to drive the system bus 24 in order to write information to the host computer memory 23. This leaves the host CPU 22 free to perform other tasks, such as image compression and decompression algorithms, as described below in more detail.

An input/output (I/O) device 25, which may be, for example, a Small Computers System Interface (SCSI) device, drives an I/O bus 27, which is interfaced to the digital storage device 30 of the present invention. One or more peripheral devices, such as a display monitor 28 and a control panel 29 may be interfaced to the system bus 24 via some other types of interface devices 26 and 31 commonly used for such peripheral devices. The host computer memory 23 stores programs that are utilized by the host CPU 22 and data, including the video image data received by the PCI/DMA device 21. The host computer memory 23, in accordance with one embodiment of the present invention, stores a compression program that is executed by the host CPU 22 in order to compress the digitized video data prior to storage in the digital storage device 30. The host computer memory 23, in accordance with this embodiment, also stores a decompression program that is executed by the host CPU 22 in order to decompress the digitized video data later read out of the digital storage device 30. An example of a suitable compression/decompression algorithm is the Moving Pictures Experts Group (MPEG) algorithm, or a version thereof.

In accordance with the embodiment of FIG. 2, the PCI/DMA device 21 receives video image frames, or portions of the image frames, in real-time from the scan converter component 6 as the scan converter component generates the video image frame data as ultrasound images are being acquired in real-time. At this time, the PCI/DMA device 21 is driving the system bus 24, which includes both the address and data bus of the personal computer 20, and writes the received digitized video image data into host computer memory device 23 in real-time as it is received. A user (not shown) operating the control panel 29 may enter information specific to the patient and to the object(s) within the patient being imaged. This information is passed along to the host CPU 22 via the I/O device 26 and the system bus 24 to the host CPU 22, preferably prior to image acquisition. Graphics and/or text overlay programs residing in the host computer memory device 23 are executed by the host CPU 22 to cause the ultrasound image data stored in the host computer memory 23 to be read out of the host memory device and overlayed with text and/or graphics information, such as, for example, header information that identifies the patient, the date of the ultrasound imaging information and the object(s), or portion of an object, being imaged. As the ultrasound video image data is processed by the host CPU 22, the processed ultrasound video image data is written into the digital storage device 30 for later retrieval and viewing.

All of these actions within the ultrasound image acquisition circuitry 10 and the PC 20 occur in real-time. Ultimately, the video data corresponding to the entire imaging session, or portions of interest thereof, will reside in the digital storage device 30. The user can customize the portions of the imaging session and the overlay information that are stored in digital storage device 30 by inputting commands at the control panel 29. The digital storage device 30 is not limited to any particular type of digital storage device. Simply put, the digital storage device 30 can be any digital storage device capable of being written to at a high enough speed to enable the real-time storage of video image data corresponding to the image acquisition session. The overlay information (e.g., the header) can be used by the host CPU 22 to later access and view the video.

Entries on the control panel 29 made by a user may also be used to commence processing and storage of the video information in the digital storage device 30, which may be, for example, the hard disk of the personal computer 20. Entries on the control panel 29 made by a user may also be used to retrieve archived video information contained in the digital storage device 30. When archived video image data is retrieved from the digital storage device 30, video output circuitry (not shown) comprised by the display monitor device 28 receives the video image data and formats the video image data in accordance with a predetermined horizontal and vertical synchronization process. The synchronization process is dictated by the type of display monitor utilized. The video output circuitry of the display monitor device 28 also translates the data into either color data or black-and-white data, depending upon the type of data stored in digital storage device 30 and the requirements of the display monitor 28. It should be noted that the display monitor device utilized for this purpose may be the display monitor device of the PC, the display monitor device of an ultrasound system, or a separate display monitor device.

In accordance with one embodiment, in addition to the host CPU 22 executing the programs described above, the host CPU 22 may compress the ultrasound video data prior to having it stored in the digital storage device 30. The compression may occur before or after the host CPU 22 overlays the video data with the aforementioned graphics and/or text information. If the information stored in the digital storage device 30 is compressed, a decompression algorithm will be performed by the host CPU 22 prior to the information being sent to the display monitor device 28. It should be noted that existing compression/decompression algorithms are available in the market that are suitable for this purpose. Compression/decompression algorithms that are proprietary or that are developed in the future may also be suitable or adaptable for use with the present invention.

Figure 3:
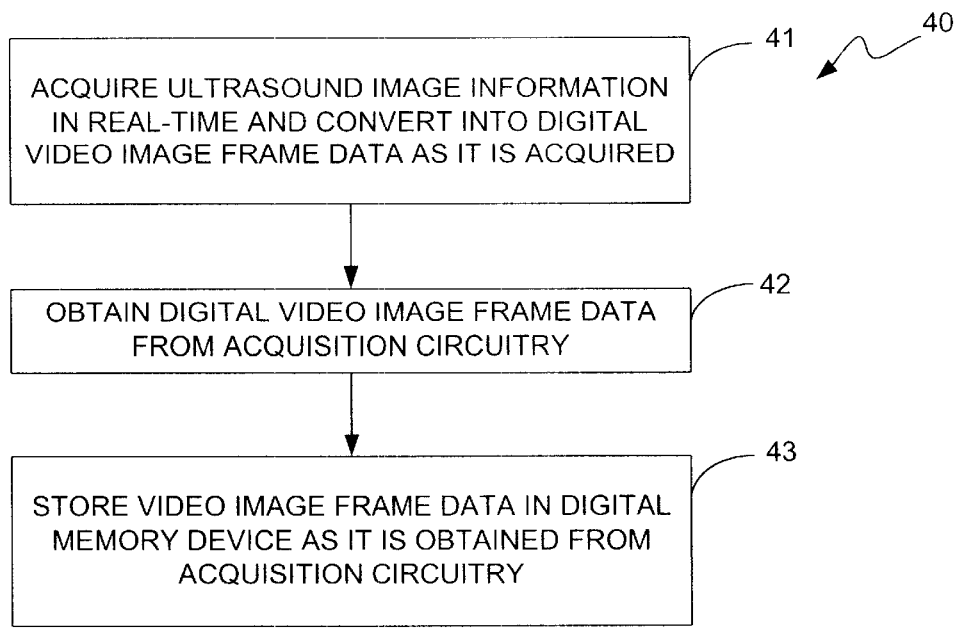
FIG. 3 is a flow chart demonstrating an example of the method performed by the system shown in FIG. 1 for storing digital ultrasound video data.
Figure 4:
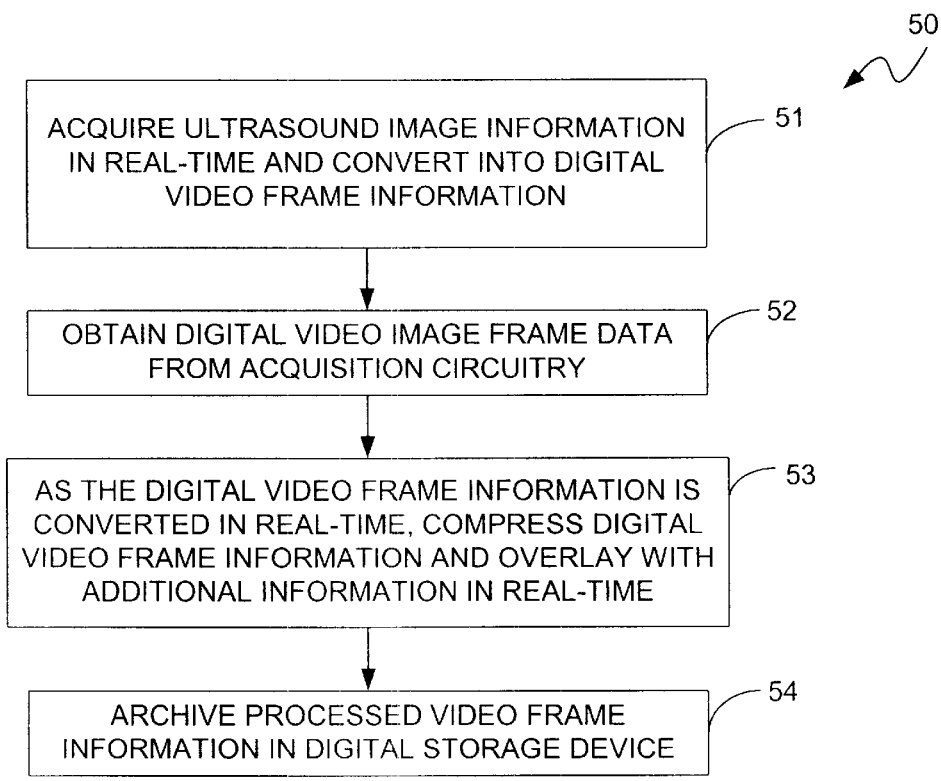
FIG. 4 is a flow chart demonstrating an example of the method performed by the system shown in FIG. 2 for storing digital ultrasound video data.

FIGS. 3 and 4 are flow charts illustrating example embodiments of the methods of the present invention for performing real-time storage of digital video ultrasound imaging data. FIG. 3 illustrates the method performed by the UIAVS system 1 of FIG. 1. In accordance with this embodiment, no compression is performed and no additional information (e.g., header, graphics, etc.) is added to the digital image frame data. The first step in the method 40 is to acquire the ultrasound image information in real-time and convert it into digital video data, as indicated by block 41. This step is performed by the ultrasound image acquisition circuitry 10. The next step is performed when the interface unit 11 obtains the digital video image frame data from the scan converter 6, which is represented by block 42. The interface unit 11 obtains the data in real-time as the pixel intensity values are set for the video image frame by the scan converter component 6. It should be noted that the interface unit 11 can obtain the data on a pixel-by-pixel basis, on a frame line-by-frame line basis, or an image frame-by-image frame basis.

As the video image frame data is obtained by the interface unit 11, the image frame data is stored in the digital memory unit 13. Storage in the digital memory device 13 can be performed on a frame pixel-by-frame pixel basis, on a frame line-by-frame line basis, or an image frame-by-image frame basis. The point here is that the digital image frame data is stored in the digital memory device 13 in real-time as the ultrasound image is acquired and converted into digital image frame data.

FIG. 4 illustrates the method performed by the UIAVS system 1 of FIG. 2. In accordance with this embodiment, compression is performed and additional information (e.g., header, graphics, etc.) is added to the digital image frame data prior to storage in the digital storage device 30, which, in this case, is the hard drive of the personal computer 20. The first step in the method 50 is to acquire the ultrasound image information in real-time and convert it into digital video data, as indicated by block 51. Again, this step is performed by the ultrasound image acquisition circuitry 10. The next step is performed when the PCI/DMA device 21 obtains, in real-time, the digital video image frame data from the scan converter 6, which is represented by block 52. The PCI/DMA device 21 can obtain the video data on a pixel-by-pixel basis, on a frame line-by-frame line basis, or an image frame-by-image frame basis.

As the digital video frame information is obtained in real-time, the digital video frame information is processed by compressing it and overlaying it with any desired archiving information in real-time. This step is represented by block 53. The processed video frame information is then stored in real-time in digital storage device 30. This step is represented by block 54.

Once the video data has been stored in the digital storage device, it can be retrieved from the digital storage device and played back on display monitor device. It is preferred that the stored video information include some type of identification information, such as the aforementioned header information, so that the videos can be easily organized and archived in memory for easy retrieval at a later time. Graphics and/or text information facilitate analysis of the played back videos in that the information can provide details relating to the image acquisition session, such as, for example, the patient's name, the portion of the bodily object imaged, the date on which the image acquisition session took place, the patient's physical condition at the time of the image acquisition session, the ultrasound equipment used to acquire the image, etc. However, even if such identification information is not used, a video corresponding to a particular patient can still be located by searching through the archives. Other techniques for making it possible to locate a video of a patient's ultrasound session include, for example, logging the storage device and location on the storage device at which the video is stored. Such a log could easily be generated and maintained, either by hand or with the aid of a computer.

Figure 5:
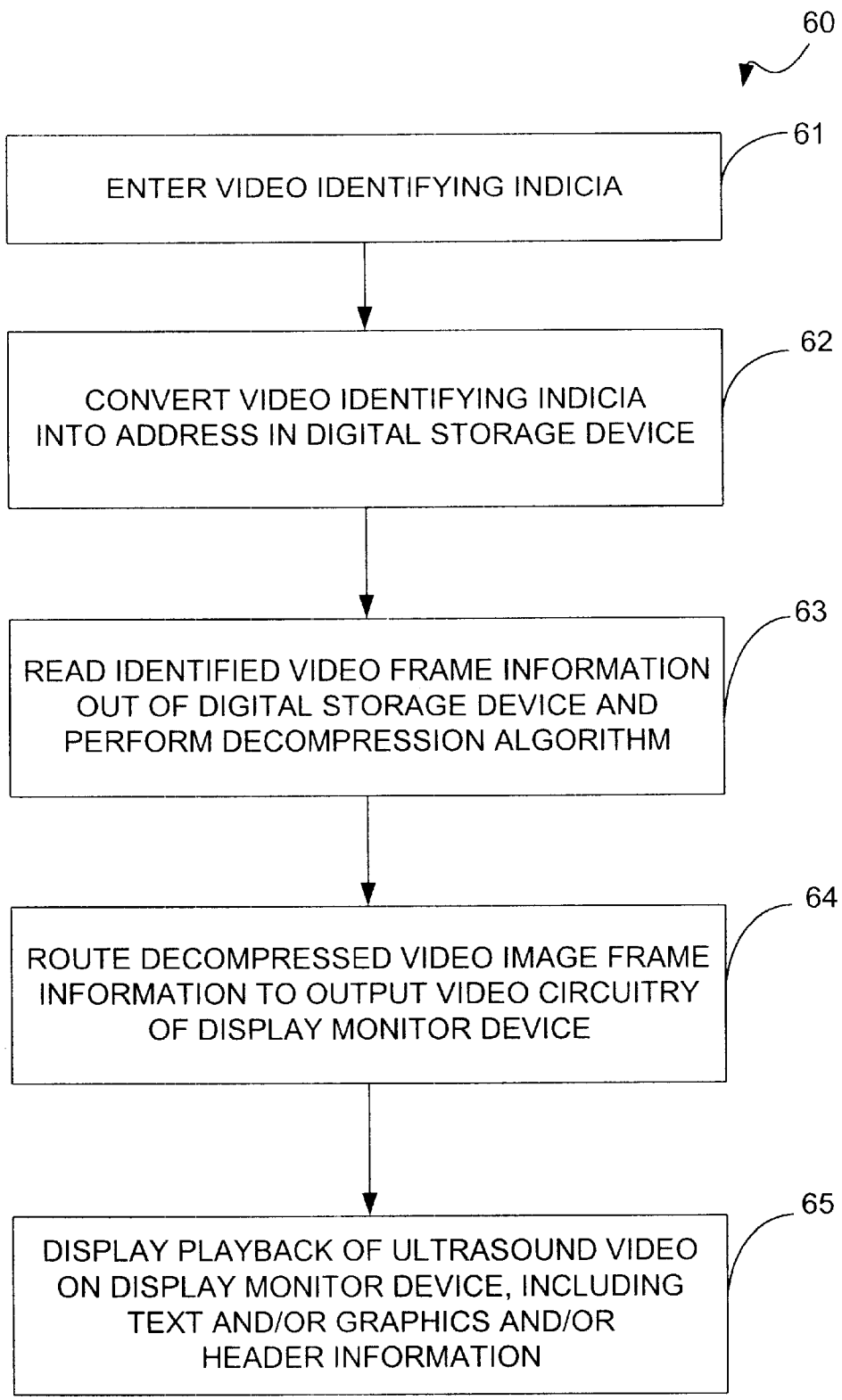
FIG. 5 is a flow chart demonstrating an example of the method performed by the system of the present invention shown in FIG. 2 in playing back a stored video of an ultrasound imaging session.

FIG. 5 is a flow chart illustrating an example of a method that may be used to invoke a playback of a video of an image acquisition session. In accordance with this example method 60, the user enters some type of information identifying the video to be played back, as indicated by block 61. The information entered by the user maybe entered via a control panel, such as control panel 29, or by some other data entry device, such as a stylus pad, for example. The information entered by the user is then converted into an address location, or a set of address locations, in the digital storage device, as indicated by block 62. The video data contained at this address or set of addresses is then read out of memory and decompressed, as indicated by block 63. The decompressed video data is then routed to the output video circuitry of a display monitor device, which formats the video image data in accordance with a predetermined horizontal and vertical synchronization process dictated by the type of display monitor device being utilized. This step is represented by block 64. The video is then played back on the display monitor device, as indicated by block 65.

One of the benefits of storing the video ultrasound information in a digitized format is that the digitized video information can be easily transferred. For example, it may be desirable for a healthcare provider at one geographic location to be able to access a patient's ultrasound video that is stored at another geographic location. With current networking technology, the digitized video could be transmitted over a network using a communications protocol such as, for example, Transfer Control Protocol over Internet Protocol (TCP/IP) to the healthcare provider's computer. The transferred video data could then be de-encapsulated, stored on the hard drive of the computer, and then displayed on the display monitor device of the computer. Those skilled in the art will, in view of the discussion provided herein, understand the many potential benefits of the present invention.

It should be noted that the present invention has been described with reference to example embodiments to which the present invention is not limited. For example, the personal computer embodiment shown in FIG. 2 is merely an example of one suitable implementation of the present invention. Those skilled in the art will understand that virtually an infinite number of variations to the embodiments described herein can be made and that all such variations are within the scope of the present invention. It should also be noted that functions described as being performed in hardware can be performed in software or in a combination of hardware and software. For example, although compression/decompression algorithms are typically performed by a processor executing software, these functions can also be performed in hardware or in a combination of hardware and software. Those skilled in the art will understand that other variations and modifications can be made to the embodiment discussed above without deviating from the scope of the present invention.

What is claimed is:

1. An ultrasound image acquisition and video storage system comprising:

an ultrasound image acquisition component, the ultrasound image acquisition component comprising logic comprised to acquire ultrasound images over a period of time and to convert the acquired ultrasound images into digital video images in real time as the images are acquired; and digital video storage logic in communication with the ultrasound image acquisition component, the digital video storage logic being configured to obtain the digital video images from the ultrasound image acquisition component and to store the video images in a digital storage device in real-time, the digital storage device being comprised by the digital video storage logic, wherein the digital video storage logic comprises a processor that synchronizes the real-time video images with a timing of the processor as said images are acquired, and that overlays the digital video images with text information relating to the acquired ultrasound images, and wherein the processor overlays the digital video images with the text information prior to storing the digital video images in the digital storage device, and wherein the text information overlayed on the digital video images is stored with the digital video images in the digital storage device.

2. The system of claim 1, wherein the text information includes information relating to an object within a patient's body.

3. The system of claim 2, wherein the text information includes information relating to an identity of the patient.

4. An ultrasound image acquisition and video storage system comprising:

an ultrasound image acquisition component, the ultrasound image acquisition component comprising logic comprised to acquire ultrasound images over a period of time and to convert the acquired ultrasound images into digital video images in real time as the images are acquired; and digital video storage logic in communication with the ultrasound image acquisition component, the digital video storage logic being configured to obtain the digital video images from the ultrasound image acquisition component and to store the video images in a digital storage device in real-time, the digital storage device being comprised by the digital video storage logic, wherein the digital video storage logic comprises a processor that synchronizes the real-time video images with a timing of the processor as said images are acquired, and that overlays the digital video images with graphics information prior to storing the digital video images in the digital storage device, and wherein the graphics information is overlayed on the digital video images in the digital storage device.

5. The system of claim 4, wherein the graphics information includes information intended to assist a person in analyzing the digital video images.

6. The system of claim 1, wherein the processor comprising the digital video storage logic executes a compression algorithm on the digital video images as they are obtained so that the digital video images stored in the digital storage device are compressed.

7. The system of claim 1, further comprising:

a display monitor device, and wherein the processor comprising the digital storage logic is capable of being configured to reread the stored digital video images out of the digital storage device and cause the digital video images to be displayed on the digital display monitor device.

8. The system of claim 1, wherein the processor comprising the digital video storage logic is a personal computer including a central processing unit (CPU), and wherein the digital storage device is a hard drive of the personal computer.

9. The system of claim 1, wherein a personal computer comprises the digital video storage logic, and wherein the processor includes a central processing unit (CPU), and wherein the digital storage device is a hard drive external to the personal computer and in communication with the personal computer.

10. The system of claim 9, wherein the personal computer comprises a display monitor device, and wherein the CPU is capable of being configured to read the stored digital video images out of the hard drive and cause the digital video images to be displayed on the display monitor device.

11. A method for storing digital video ultrasound images, the method comprising the steps of:
  acquiring ultrasound images over a period of time:
    converting the acquired ultrasound images into digital video images in real-time as the images are acquired, said converting occurring in synchronism with a timing control of a processor;
    storing the digital video images in a digital storage device in real-time, further comprising the step of:
      overlaying the digital video images with text information relating to the acquired ultrasound images prior to storing the digital video images in the digital storage device, and wherein the text information overlayed on the digital video images is stored with the digital video images in the digital storage device.

12. The method of claim 11, wherein the text information includes information relating to an object within a patient's body.

13. The method of claim 12, wherein the text information includes information relating to an identity of the patient.

14. A method for storing digital video ultrasound images, the method comprising the steps of:
  acquiring ultrasound images over a period of time:
    converting the acquired ultrasound images into digital video images in real-time as the images are acquired, said converting occurring in synchronism with a timing control of a processor;
    storing the digital video images in a digital storage device in real-time, further comprising the step of:
      overlaying the digital video images with graphics information relating to the acquired ultrasound images prior to storing the digital video images in the digital storage device, and wherein the graphics information overlayed on the digital video images is stored with the digital video images in the digital storage device.

15. The method of claim 14, wherein the graphics information includes information intended to assist a person in analyzing the digital video images.

16. The method of claim 11, further comprising the step of compressing the digital video images as they are obtained so that the digital video images stored in the digital storage device are compressed.

17. The method of claim 11, further comprising the step of:
  reading the stored digital video images out of the digital storage device and displaying the digital video images on a display monitor device.

18. The method of claim 11, wherein the step of acquiring the ultrasound images into digital video images is performed by an ultrasound image acquisition system of an ultrasound system, and wherein the step of storing the digital video images is performed by said processor, which said processor includes a central processing unit and is constructed within a personal computer, and wherein the digital storage device is a hard drive of the personal computer.

19. The method of claim 18, wherein the personal computer comprises a display monitor device, and wherein the method further comprises the step of:
  reading the stored digital video images out of the hard drive and displaying the digital video images on the display monitor device.

20. A program storage device readable by a computer processor, tangibly embodying a computer program for storing digital video ultrasound images, the computer program comprising:
  a first code segment, the first code segment acquiring ultrasound images over a period of time:
    a second code segment, the second code segment converting the acquired ultrasound images into digital video images in real-time as the images are acquired, said converting occurring in synchronism with a timing control of the computer processor controlling the computer program;
    a third code segment, the third code segment storing the digital video images in a digital storage device in real-time, wherein the second code segment overlays the digital video images with text information relating to the acquired ultrasound images prior to the third code segment storing the digital video images in the digital storage device.

21. The computer program of claim 20, wherein the second code segment overlays the digital video images with graphics information relating to the acquired ultrasound images prior to the third code segment storing the digital video images in the digital storage device.

22. The computer program of claim 20, wherein the second code segment compresses the digital video images such that the digital video images stored by the third code segment are compressed.

* * * * *